United States Patent [19]

Cone et al.

[11] Patent Number: 5,047,510

[45] Date of Patent: Sep. 10, 1991

[54] METHOD OF PURIFICATION OF TRANSFORMING GROWTH FACTOR-BETA

[75] Inventors: James L. Cone, Germantown, Md.; Joseph E. DeLarco, Chesterfield, Mo.

[73] Assignee: Ostuka Pharmaceutical Co. Ltd., Tokyo, Japan

[21] Appl. No.: 420,704

[22] Filed: Oct. 11, 1989

Related U.S. Application Data

[63] Continuation of Ser. No. 141,382, Jan. 7, 1988, abandoned.

[51] Int. Cl.$^5$ .......................... C07K 3/02; C07K 3/22; C07K 3/28
[52] U.S. Cl. .................................. 530/399; 530/412; 530/415; 530/416; 530/424
[58] Field of Search ............... 530/399, 412, 415, 416, 530/422, 424

[56] References Cited

FOREIGN PATENT DOCUMENTS 0186994  10/1984  Japan .

OTHER PUBLICATIONS

Roberts et al., *Biochemistry* 22 (25), 1983, 5692, pp. 5692–5698.
Roberts et al., *PNAS* 77 (6), 1980, pp. 3494–3498.
Sofer et al., *Bio Techniques*, Nov./Dec. 1983, pp. 198–203.
Bonnerjea et al., *Bio Technology*, vol. 4, 1986, pp. 954–958.
Seyedin et al., *JBC* 261, 1986, pp. 5693–5695.
Marquardt et al., *PNAS* 80, 1983, pp. 4684–4688.
Twardzik et al., *PNAS* 82, 1985, pp. 5300–5304.
Cheifetz et al., *Cell*, vol. 48, 1987, pp. 409–415.
Frolik et al., Am Soc Biol Chem 74th Meeting, 1983, #440.
Bio-Rad Bulletin 1153.

*Primary Examiner*—F. T. Moezie
*Assistant Examiner*—Andrew G. Rozycki
*Attorney, Agent, or Firm*—Sughrue, Mion, Zinn, Macpeak & Seas

[57] ABSTRACT

The present invention relates to improved methods for purifying TGF-beta so as to obtain such in high yields. The process steps consist of acid-ethanol extracting platelets, cation exchange separation, and hydrophobic separation.

10 Claims, 1 Drawing Sheet

5,047,510

METHOD OF PURIFICATION OF TRANSFORMING GROWTH FACTOR-BETA

This is a continuation of application Ser. No. 07/141,382, filed Jan. 7, 1988 which is abandoned.

FIELD OF THE INVENTION

The present invention relates to methods for purifying transforming growth factor-$\beta$ (hereinafter "TGF-$\beta$").

BACKGROUND OF THE INVENTION

Extracts of human platelets contain many growth factors. The isolation and characterization of these factors, as well as their interactions, are currently active areas of investigation. The growth factor, TGF-$\beta$ was originally purified from the acid-ethanol extracts of human platelets (see Assoian. R. K. et al, *J. Biol. Chem.*, 258:7155–7160 (1983)). This method takes advantage of the anomalous chromatographic behavior of TGF-$\beta$ on a Bio-Gel P60 molecular weight sizing column equilibrated with 1.0M acetic acid (pH 2.7) in the presence or absence of 8.0M urea. That is, TGF-$\beta$ elutes much later than anticipated when run in 1.0M acetic acid (pH 2.7), but returns to an expected elution volume in the presence of 8.0M urea in 1.0M acetic acid (pH 2.7). This method has also been modified to include a hydrophobic HPLC step using a $C_{18}$ resin (Synchropak) (see Derynck, R. et al. *Nature*, 316:701–705 (1985)). However, these methods are disadvantageous because they are time consuming and produce a low yield.

Cartilage-inducing factor-$\beta$ (hereinafter "CIF-$\beta$"), is a factor which is closely related to TGF-$\beta$ in many respects, e.g., sequence homology and activity (see Seyedin, S. M. et al. *Proc. Natl. Acad. Sci., USA*, 82:2267–2271 (1985); Seyedin. S. M. et al. *J. Biol. Chem.*, 261:5693–5695 (1987); and Seyedin, S. M. et al. *J. Biol. Chem.*, 262:1946–1949 (1987)). A cation-exchange resin. Whatman CM-52, has been used in the purification of CIF-$\beta$. This resin has also been used in the isolation of TGF-$\beta$ from demineralized bone. A similar cation-exchange resin (i.e.. a CM-Triacryl M resin obtained from LKB) has been used in combination with a Bio-Gel P30 molecular weight sizing column and two HPLC steps, one step using a $C_{18}$ resin and the other step using a CN resin, in the purification of TGF-$\beta$ from bovine kidney (see Roberts, A. B. et al. *Biochem.*, 22:5692–5698 (1983)). However, these methods are disadvantageous because they produce low yields.

Conditioned media also contains many growth factors. The isolation and characterization of these growth factors, as well as their interactions, are also currently active areas of investigation. The growth factor, TGF-$\beta$ has been purified from conditioned media (see DeLarco, J. E. et al. *Proc. Natl. Acad. Sci. USA*, 82:5015–5019 (1985). This method involves lyophilizing conditioned media, extracting such with 1.0M acetic acid and carrying out sizing chromatography on the clarified extract on a Bio-Gel P30 molecular weight sizing column. This method is disadvantageous because it is time consuming and produces a low yield.

SUMMARY OF THE INVENTION

Accordingly, an object of the present invention is to provide methods for purifying TGF-$\beta$ in high yields.

Another object of the present invention is to provide methods for purifying TGF-$\beta$ more rapidly with a minimum number of operations.

The above-described objects of the present invention have been met by a method for purifying TGF-$\beta$ comprising:

(1) acid-ethanol extracting platelets;

(2) carrying out cation-exchange separation on the resulting extract of step (1) and isolating the fraction(s) containing TGF-$\beta$ activity; and (3) carrying out hydrophobic separation on the fraction(s) containing TGF-$\beta$ activity of step (2) and isolating the fraction(s) containing TGF-$\beta$ activity, so as to obtain TGF-$\beta$ purified to homogeneity as determined by SDS-polyacrylamide gel electrophoresis.

The above-described objects of the present invention have also been met by a method for purifying TGF-$\beta$ comprising:

(1) carrying out cation-exchange separation on conditioned media containing TGF-$\beta$ and isolating the fraction(s) containing TGF-$\beta$ activity; and (2) carrying out hydrophobic separation on the fraction(s) containing TGF-$\beta$ activity on step (1) and isolating the fraction(s) containing TGF-$\beta$ activity, so as to obtain TGF-$\beta$ purified to homogeneity as determined by SDS-polyacrylamide gel electrophoresis.

DETAILED DESCRIPTION OF THE INVENTION

Figure 1:
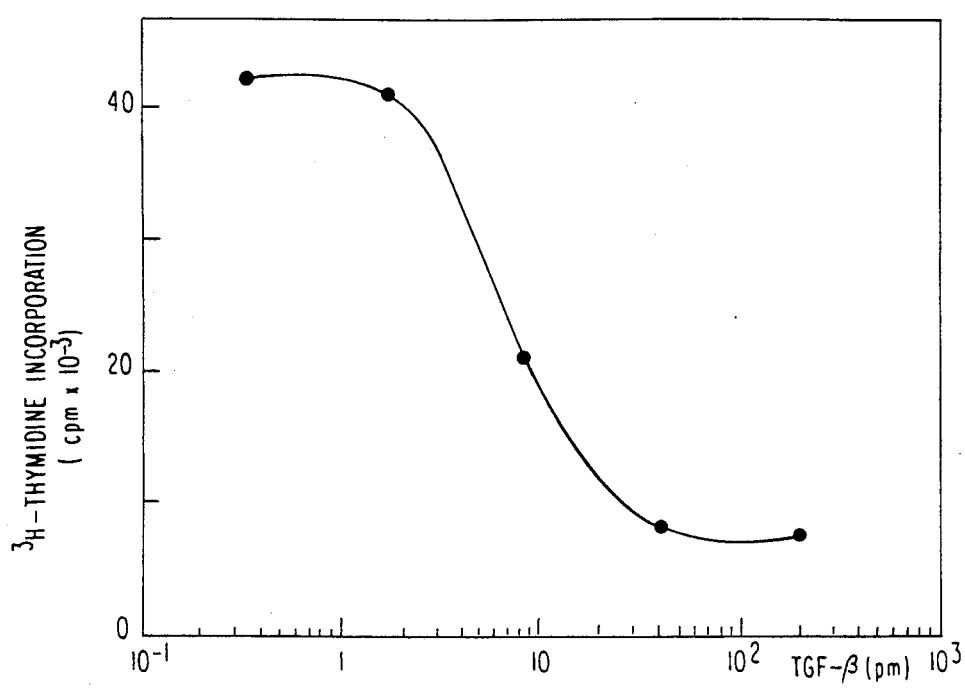
FIG. 1 shows the inhibition of $^3$H-Thymidine incorporation in mink lung epithelial cells (ATCC No. CCL-64) caused by TGF-$\beta$.

As discussed above, the above-described objects of the present invention have been met by a method for purifying TGF-$\beta$ comprising:

(1) acid-ethanol extracting platelets;

(2) carrying out cation-exchange separation on the resulting extract of step (1) and isolating the fraction(s) containing TGF-$\beta$ activity; and (3) carrying out hydrophobic separation on the fraction(s) containing TGF-$\beta$ activity of step (2) and isolating the fraction(s) containing TGF-$\beta$ activity, so as to obtain TGF-$\beta$ purified to homogeneity as determined by SDS-polyacrylamide gel electrophoresis.

The above-described objects of the present invention have also been met by a method for purifying TGF-$\beta$ comprising:

(1) carrying out cation-exchange separation on conditioned media containing TGF-$\beta$ and isolating the fraction(s) containing TGF-$\beta$ activity; and (2) carrying out hydrophobic separation on the fraction(s) containing TGF-$\beta$ activity of step (1) and isolating the fraction(s) containing TGF-$\beta$ activity, so as to obtain TGF-$\beta$ purified to homogeneity as determined by SDS-polyacrylamide gel electrophoresis.

The treatment of the platelets in the purification procedure of the present invention is much simpler compared to the known methods described above (see Assoian, R. K. et al. *J. Biol. Chem.*, 258:7155–7160 (1983)

and Derynck. R. et al. *Nature,* 316:701-705 (1985)) in that there is no need in the present invention to remove cell contamination or excess plasma. Further, although the total amount of protein varies considerably in the crude acid-ethanol extract and is primarily a function of the red blood cell contamination, this has not been found to cause any problems in the subsequent steps of the purification, i.e., since the first separation step utilizes a high capacity cation-exchange resin, the total protein is a secondary consideration to the optimal release of the TGF-$\beta$ present.

Similarly, the treatment of conditioned media in the purification procedure of the present invention is much simpler compared to the known methods described above (DeLarco, J. E. et al, *Proc. Natl. Acad. Sci. USA,* 82:5015-5019 (1985)) in that there is no need in the present invention for lyophilization or clarification.

As discussed above, TGF-$\beta$ can be obtained from platelets or from conditioned media. As used herein, "conditioned media" is media in which cells have been previously grown and which contains secreted factors, including TGF-$\beta$, from the cells. The conditioned media is preferably low serum or serum free in order to avoid the presence of additional proteins found in the serum. The particular cell which secretes TGF-$\beta$ is not critical to the present invention. Examples of cells which secrete TGF-$\beta$ into media include the human melanoma cell line M3827 (ATCC No. CRL-9193), the African green monkey kidney epithelial cell line BSC-1 (Ristow. H.-J., *Proc. Natl. Acad. Sci. USA,* 83:5531-5533 (1986)) and the normal rat kidney cell line NRK-49F (ATCC No. CRL-1570).

The amount of platelets employed is not critical to the present invention. Generally, the platelets are employed in an amount of about 100-500 units, preferably about 100-300 units. The amount of conditioned media employed is also not critical to the present invention.

The acid-ethanol extraction of platelets is generally carried out at a pH of about 4.0 or less, preferably about 3.5 to about 2.0 and at an ethanol concentration of not less than about 50% (v/v). preferably about 80% (v/v) to about 70% (v/v). The acid-ethanol combination allows for both disruption of the platelets and release of soluble proteins such as TGF-$\beta$.

Prior to carrying out cation-exchange separation, the acid-ethanol extract and the conditioned media should be adjusted to a pH of about 5.5. i.e., the pH of the buffer which is employed to equilibrate the cation-exchange resin.

The purification of TGF-$\beta$ is carried out by a unique series of separation steps. One separation step is based on cation-exchange and another separation step is based on hydrophobicity.

The particular cation-exchange resin is not critical to the present invention. For example, cation-exchange separation can be carried out using a TSK SP-5PW cation-exchange resin, a Pharmacia Mono-S cation-exchange resin, Whatman CM-52 cellulose. Whatman sulfoethyl cellulose or a Zeta-preparation cartridge. In the present invention, cation-exchange separation using a TSK SP-5PW cation-exchange resin is preferred because of its high resolution and large capacity.

Similarly, the particular hydrophobic resin is not critical to the present invention. For example, hydrophobic separation can be carried out using, for example, a number of reverse phase resins such as $C_4$, $C_6$, $C_8$, $C_{18}$, etc. In the present invention, $C_4$ HPLC chromatography is preferred because it gives excellent resolution in the separation of TGF-$\beta$ activity from other activities released by platelets or found in conditioned media. This method also allows rapid separation, i.e., in a matter of minutes, rather than hours or days.

TGF-$\beta$ activity can be assayed using mink lung epithelial cells (ATCC No. CCL-64) maintained in Dulbecco's Modified Eagle's medium (GIBCO) (hereinafter "DMEM") containing 10% (v/v) fetal calf serum (HyClone). More specifically, the cells are released from tissue culture plates by the addition of 0.05% (w/v) trypsin. 0.1% (w/v) EDTA in phosphate buffered saline without calcium and magnesium and 0.5 ml of the resulting cells, at about $5 \times 10^4$ cells per ml, are seeded in 48-well tissue culture plates. Aliquots of a TGF-$\beta$ standard and the unknown samples to be assayed are added at this time. After a 24 hour incubation at 37° C. in a 95% air (v/v)/5% $CO_2$ (v/v) atmosphere, the wells are pulsed with 50 $\mu$l of 0.01 miCi/ml $^3$H-thymidine (New England Nuclear, specific activity 6.7 Ci/mM). Approximately 16 hours later, the wells are washed with DMEM three times followed by two washes with cold 10% (w/v) trichloroacetic acid. After removal of the trichloroacetic acid, 0.5 ml of 1.0N NaOH are added to lyse the cells and 450 $\mu$l of the lysed cells are removed for counting in a liquid scintillation counter.

The above assay is based on the observation that monolayer growth of the mink lung epithelial cells is inhibited in the presence of TGF-$\beta$ (see Holley, R. W. et al, *Cell Bio. Int. Rep.,* 7:141-147 (1983) and Tucker, R. F. et al, *Proc. Natl. Acad. Sci., USA,* 81:6757-6761 (1984)). The use of the mink lung epithelial cells with their high sensitivity to TGF-$\beta$ (see Chinkers, M., *J. Cell. Physiol.,* 130:1-5 (1987)) in a $^3$H-thymidine incorporation assay has been found to be a simple, reproducible and quantitative assay as shown in FIG. 1. Note, in FIG. 1, duplicate wells were carried out for each concentration and there was less than 10% error at all points.

Other $^3$H-thymidine based assays for TGF-$\beta$ activity have been reported and can also be employed in the present invention (see Assoian, R. K. et al, *J. Biol. Chem.,* 258:7155-7160 (1983) and Chinkers, M., *J. Cell. Physiol.,* 130:1-5 (1987)).

TGF-$\beta$ is useful for wound healing and tissue repair (European Patent Application Publication Nos. 0121849 and 0200341).

The following examples are provided for illustrative purposes only and are in no way intended to limit the scope of the present invention.

EXAMPLE

A. Platelet Extraction 200 clinically outdated units of platelets obtained from the Red Cross in Washington, D.C. were employed. The cells were pelleted by centrifugation in 250 ml conical tubes at 3,000 rpm for 25 minutes at 20° C. After decanting the plasma, 4 volumes of an acid-ethanol solution comprising 70% (v/v) ethanol and 0.05M HCl (pH 1.9), were added per volume of cell pack. The resulting suspension has a pH of approximately 3.5. The suspension was thoroughly vortexed, pooled and left overnight at 4° C. The suspension was then centrifuged at 19,000 rpm in a Beckman Type 19 rotor for 45 minutes at 10° C. The supernatant was collected and the pH was adjusted to 5.5 with NaOH. The ethanol was removed by rotary evaporation and the precipitate that formed was removed by centrifugation in a 50.2 Ti rotor at 35,000 rpm for 30 minutes at 10° C. The resulting crude extract, a total of 675 ml, contained a total of 877 mg of protein. The amount of protein was determined by the Bradford method (see Bradford, M. M., *Anal. Biochem.*, 72:248-254 (1976)) using bovine serum albumin as the standard. The TGF-$\beta$ activity of this crude extract was determined and it was found that there was 1.7 mg of TGF-$\beta$ present. This number is determined by extrapolation of the amount of sample used compared to the 50% inhibition point of the standard curve of purified TGF-$\beta$ (see FIG. 1). This point is usually around 0.2 ng/ml (8.0 pm), as shown in FIG. 1.

B. Cation-Exchange Separation

Figure 2:
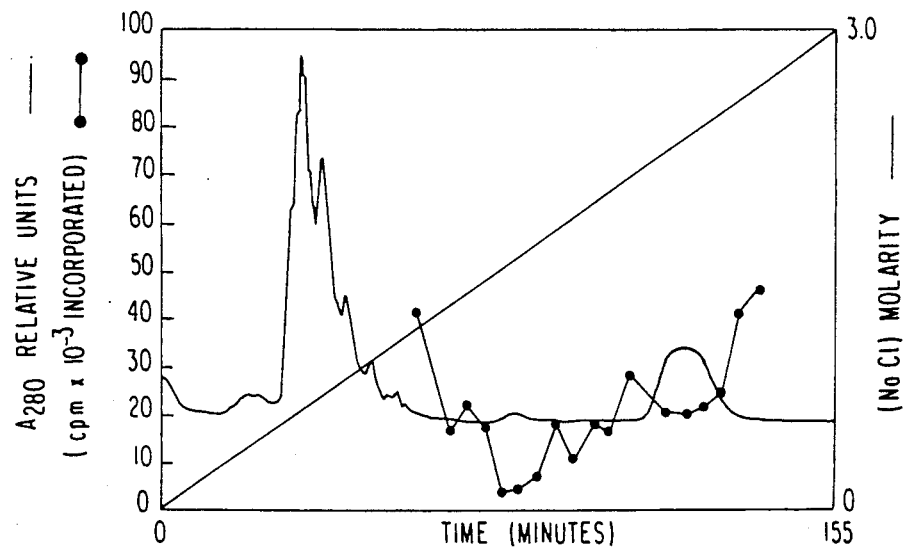
FIG. 2 shows cation-exchange chromatography of an acid-ethanol extract of platelets on a TSK SP-5PW column.

The resulting crude extract was then loaded onto a preparative TSK SP-5PW column (5.5 cm $\times$ 20 cm with a 4.5 cm $\times$ 5 cm guard column) that had previously been equilibrated with 0.025M sodium acetate (pH 5.5). A linear 0 to 3.0M NaCl gradient in 0.025M sodium acetate (pH 5.5) was developed over 155 minutes. The flow rate was 25 ml/min and the fractions were collected every two minutes. The elution profile and TGF-$\beta$ activity, measured using the mink lung epithelial cells as described above, from the TSK SP-5PW column is shown in FIG. 2. In FIG. 2, the relative absorbance at $A_{280}$ is shown by a solid line. The solid line connecting closed circles is the TGF-$\beta$ activity.

FIG. 2 shows that elution of TGF-$\beta$ from the TSK SP-5PW column occurs at approximately 1.5M NaCl in an area that is well separated from the major protein peaks. (Note, 100-500 units of platelets have also been loaded on the TSK SP-5PW column and the general elution profile has been found to be reproducible.) Fractions 37-45 (450 ml) in FIG. 2 were found to contain the most TGF-$\beta$ activity and when pooled found to contain 0.9 mg of TGF-$\beta$. The total protein in this pool was 5.0 mg.

C. Hydrophobic Separation

The pooled fractions containing TGF-$\beta$ activity, i.e., fractions 37-45, from the cation-exchange column described above were acidified to pH 2.5 with 6.0M HCl and applied directly to a C$_4$ (Vydac, 214TP510) semi-preparative HPLC column. Vydac C$_4$ HPLC consists of a C$_4$(—(CH$_2$)$_3$—CH$_3$) hydrophobic bonded phase on a 300 Å pore-size 10$\mu$ spherical silica bead. The column was run at 3.0 ml per minute with two buffers, i.e., buffer (A) comprising 0.1% (v/v) trifluoroacetic acid (hereinafter "TFA") in water and buffer (B) comprising 0.1% (v/v) TFA in 100% (v/v) acetonitrile. The gradient in the column was from 100-72% buffer (A)/0-28% buffer (B) over 15 minutes and from 72%-60% buffer (A)/28-40% buffer (B) at a 0.25% per minute increase in buffer (B). The fractions were collected every minute and monitored by absorbance at $A_{206}$. The results are shown in FIG. 3.

Figure 3:
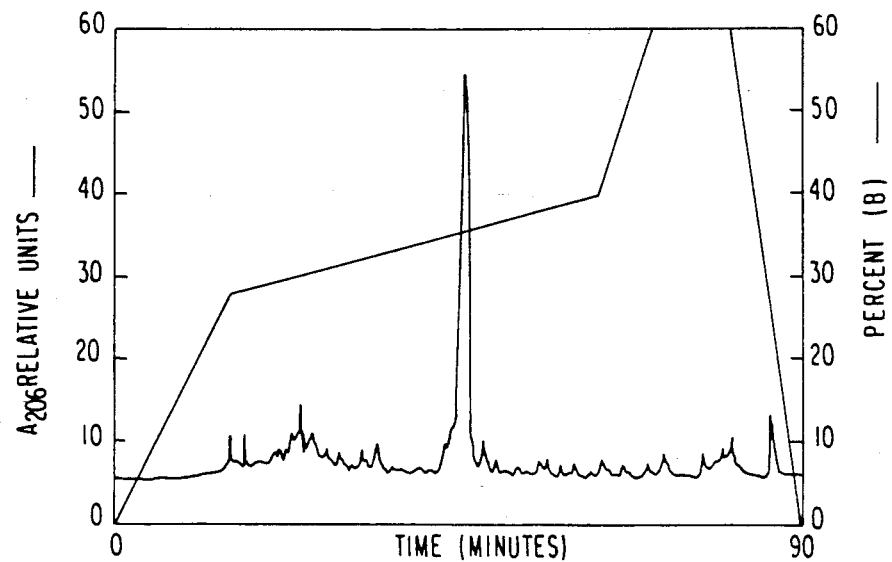
FIG. 3 shows hydrophobic chromatography of the TGF-$\beta$ containing fractions, obtained from the TSK SP-5PW column of FIG. 2, on a Vydac $C_4$ semi-prep HPLC column.

As shown in FIG. 3, the elution of the major protein fraction occurred at approximately 36% (v/v) acetonitrile. Note, with column degradations through use, early elution and minor contamination of the product from adjacent peaks is seen.

The two central fractions from the peak shown in FIG. 3 were pooled and when assayed for TGF-$\beta$ activity were found to contain 0.5 mg of TGF-$\beta$. Thus, using the process of the present invention, the 200 units of platelets gave an overall yield of 30% TGF-$\beta$ with 2.5 $\mu$g of TGF-$\beta$ per unit of platelets and the half maximal inhibition point in the assay using mink lung epithelial cells was approximately 8.0 pm. This is compared to a yield of 0.5 $\mu$g of TGF-$\beta$ per unit of platelets with similar activity using previous isolation techniques. Hence, the recovery in the present invention is 5 fold increased over that of previous isolation techniques (see Assoian, R. K. et al, *J. Biol. Chem.*, 258:7155-7160 (1983) and Derynck, R. et al, *Nature*, 316:701-705 (1985)).

D. Purity Analysis

An aliquot from the pooled peak shown in FIG. 3, representing 5.0 $\mu$g of protein, was reduced using 5.0% (v/v) 2-mercaptoethanol. Then, the reduced and a similar non-reduced sample were electrophoresed on a 12% (w/v) SDS-polyacrylamide gel prepared as described in Laemmli, U.K., *Nature*, 227:680-685 (1970). The gels were stained with Coomasie brilliant blue R-250 (see Weber, K. et al, *J. Biol. Chem.*, 244:4406-4412 (1969)) or silver stained (BioRad). No contaminants were found with either the Coomasie blue stain or silver staining. At this level of protein in the gel, a contaminant of much less than 10% would be noted. The SDS-polyacrylamide gel electrophoresis demonstrated that the TGF-$\beta$ obtained by the method of present invention was homogeneous and greater than 90% pure.

While this invention has been described in detail and with reference to specific embodiments thereof, it will be apparent to one skilled in the art that various changes and modifications could be made therein without departing from the spirit and scope thereof.

We claim:
1. A method for purifying TGF-$\beta$ consisting essentially of:
   (1) acid-ethanol extracting platelets:
   (2) carrying out cation-exchange separation on the resulting extract of step (1) and isolating the fraction(s) containing TGF-$\beta$ activity: and
   (3) carrying out hydrophobic separation on the fraction(s) containing TGF-$\beta$ activity of step (2) and isolating the fraction(s) containing TGF-$\beta$ activity, so as to obtain TGF-$\beta$ purified to homogeneity as determined by SDS-polyacrylamide gel electrophoresis.

2. The method of claim 1, wherein said platelets are employed in an amount of 100 units to 500 units.

3. The method of claim 2, wherein said platelets are employed in an amount of 100 units to 300 units.

4. The method of claim 1, wherein said acid-ethanol extraction is carried out at a pH of less than about 4.0.

5. The method of claim 4, wherein said acid-ethanol extraction is carried out at a pH of about 3.5 to about 2.0.

6. The method of claim 1, wherein said acid-ethanol extraction is carried out at not less than about 50% (v/v) ethanol.

7. The method of claim 6, wherein said acid-ethanol extraction is carried out at about 80% (v/v) to about 70% (v/v) ethanol.

8. A method of purifying TGF-$\beta$ consisting essentially of:
   (1) carrying out cation-exchange separation on conditioned media containing TGF-$\beta$ and isolating the fraction(s) containing TGF-$\beta$ activity; and
   (2) carrying out hydrophobic separation on the fraction(s) containing TGF-$\beta$ activity of step (1) and isolating the fraction(s) containing TGF-$\beta$ activity, so as to obtain TGF-β purified to homogeneity as determined by SDS-polyacrylamide gel electrophoresis.

9. The method as claimed in claim 8, wherein said conditioned media is serum free conditioned media.

10. The method as claimed in claim 9, wherein said conditioned media has been conditioned by cells selected from the group consisting of the human melanoma cell line M3827 (ATCC No. CRL-9193), the African green monkey kidney epithelial cell line BSC-1 and the normal rat kidney cell line NRK-49F (ATCC No. CRL-1570).

* * * * *